(12) United States Patent
Kulkarni (10) Patent No.: US 7,521,248 B2
(45) Date of Patent: Apr. 21, 2009

(54) APO B MEASUREMENT SYSTEM AND METHOD

(75) Inventor: Krishnaji Kulkarni, Birmingham, AL (US)

(73) Assignee: Atherotech, Inc., Birmingham, AL (US)

( * ) Notice: Subject to any disclaimer, the term of this patent is extended or adjusted under 35 U.S.C. 154(b) by 157 days.

(21) Appl. No.: 11/788,805

(22) Filed: Apr. 20, 2007

(65) Prior Publication Data

US 2008/0261313 A1   Oct. 23, 2008

(51) Int. Cl.
G01N 33/92 (2006.01)
G01N 35/08 (2006.01)

(52) U.S. Cl. .............................. 436/71; 436/63; 436/52; 436/174; 436/177; 422/68.1; 422/81

(58) Field of Classification Search .................... 436/8, 436/13, 63, 71, 52, 174, 177; 422/68.1, 72, 422/81
See application file for complete search history.

(56) References Cited

U.S. PATENT DOCUMENTS

| | | | |
|---|---|---|---|
| 4,022,575 A | 5/1977 | Hansen et al. | |
| 4,071,324 A | 1/1978 | Reid | |
| 4,135,881 A | 1/1979 | Bakx et al. | |
| 4,224,033 A | 9/1980 | Hansen et al. | |
| 4,314,824 A | 2/1982 | Hansen et al. | |
| 4,520,108 A | 5/1985 | Yoshida et al. | |
| 4,521,519 A * | 6/1985 | Draeger et al. ................ | 436/17 |
| 4,595,496 A | 6/1986 | Carson | |
| 4,610,544 A | 9/1986 | Riley | |
| 4,742,716 A | 5/1988 | Ruzicka et al. | |
| 4,828,986 A * | 5/1989 | Smith et al. ................ | 435/7.94 |
| 4,952,372 A | 8/1990 | Huber | |
| 5,064,769 A * | 11/1991 | Gambert et al. ............. | 436/516 |
| 5,080,866 A | 1/1992 | Petty et al. | |
| 5,105,851 A | 4/1992 | Fogelman | |
| 5,108,928 A | 4/1992 | Menard et al. | |
| 5,168,067 A | 12/1992 | Miller et al. | |
| 5,171,530 A | 12/1992 | Pennatto | |
| 5,180,679 A * | 1/1993 | Schmidtberger ............ | 436/518 |
| 5,221,519 A | 6/1993 | Wuerschum | |
| 5,240,856 A | 8/1993 | Goffe et al. | |
| 5,262,049 A | 11/1993 | Ferkany | |
| 5,284,773 A | 2/1994 | Kulkarni et al. | |
| 5,286,652 A | 2/1994 | James et al. | |
| 5,384,093 A | 1/1995 | Ootani et al. | |
| 5,456,882 A | 10/1995 | Covain | |
| 5,468,643 A | 11/1995 | Su et al. | |
| 5,633,168 A * | 5/1997 | Glasscock et al. ............. | 436/52 |
| 6,121,249 A * | 9/2000 | Weissman et al. ............. | 514/52 |
| 6,753,185 B2 * | 6/2004 | Macfarlane et al. ........... | 436/71 |
| 7,098,936 B2 | 8/2006 | Cole et al. | |
| 7,166,469 B2 | 1/2007 | Holvoet et al. | |
| 2003/0119194 A1 | 6/2003 | Otvos | |

(Continued)

OTHER PUBLICATIONS

Kulkarni et al. "Quantification of cholesterol in all lipoprotein classes by the VAP-II method"—Journal of Lipid Research vol. 35, 1994 159-168..

(Continued)

Primary Examiner—Maureen M Wallenhorst
(74) Attorney, Agent, or Firm—DLA Piper LLP (US)

(57) ABSTRACT

A system and method for measuring apolipoprotein $B_{100}$ (apo B) during the cholesterol subclass measurement process is provided which obviates the need for a separate apo B test.

17 Claims, 7 Drawing Sheets

U.S. PATENT DOCUMENTS

2003/0124743 A1   7/2003   Kundu
2008/0153171 A1*  6/2008   Liu et al. .................. 436/71

OTHER PUBLICATIONS

[1] Grundy SM. Low-density lipoprotein, non-high-density lipoprotein, and apolipoprotein B as targets of lipid-lowering therapy. Circulation 2002;106:2526-2529.
[2] Ridker PM, Rifai N, Cook NR, Bradwin G, Buring JE. Non-HDL cholesterol, apolipoproteins A-I and B100, standard lipid measures, lipid ratios, and CRP as risk factors for cardiovascular disease in women. JAMA 2005;294:326-33.
[3] Pischon T, Girman CJ, Sacks SM, Rifai N, Stampfer M, Rimm EB. Non-high density lipoprotein cholesterol and apolipoprotein B in the prediction of coronary heart disease in men. Circulation 2005; 112:3375-3383.
[4] Expert panel on detection, evaluation, and treatment of high blood cholesterol in adults. Executive summary of the Third report of the National Cholesterol Education Program (NCEP) Expert panel on detection, evaluation, and treatment of high blood cholesterol in adults (Adult Treatment Panel III). JAMA 2001;285:2486-97.
[5] Package insert for apolipoprotein B test for Aeroset System and Architect c8000 by Diagnostics (2004, p. 4).
[6] Northwest Lipid Research Laboratories (NWLRL) test report for apolipoprotein B (2002).
[7] Laboratory Procedure for apolipoprotein B by the Core Laboratory at the University of Washington, St. Louis, Mo and e-mail communications with Dr. Luzzi Veronica, Assistant Lab Director.
[8] Bhatnagar D, Durrington PN. Measurement and clinical significance of apolipoproteins A-I and B. In:Rifai N, Warnick GR, Dominiczak MH, eds. Handbook of lipoprotein testing. Washington, DC: AACC Press, 2000:287-310.
[] Bachorik, PS, Lovejoy KL, Carroll MD, et al. Apolipoprotein B and A-1 distributions in the United States, 1988-1991: results of the National Health and Nutrition Examination Survey III (NHANES III). Clin Chem 1997; 43:2364-78.
International Search Report, PCT/US08/05110, Aug. 4, 2008.
Written Opinion, PCT/US08/05110, Aug. 4, 2008.

* cited by examiner

APO B MEASUREMENT SYSTEM AND METHOD

FIELD

The present invention relates generally to a method and apparatus for determining the concentrations of apolipoprotein $B_{100}$ in blood.

BACKGROUND

It is well-known that total serum cholesterol is strongly correlated with the incidence of atherosclerosis and coronary heart disease. More recent studies also indicate that specific fractions of cholesterol are more closely associated with coronary heart disease than others. Recent studies have implicated LDL (low density lipoprotein) as the class of lipoprotein responsible for the accumulation of cholesterol in cells, whereas HDL (high density lipoprotein) has been shown to be important in the removal of excess cholesterol from cells. Thus, increased levels of LDL cholesterol have been associated with the greater risk of coronary heart disease, while a strong inverse relationship exists between HDL cholesterol and the risk of coronary heart disease.

In addition to LDL and HDL, several other lipoproteins have been shown to represent independent risk factors for coronary heart disease. Increased plasma concentrations of lipoprotein(a) [Lp(a)], a cholesterol rich lipoprotein, has been observed in survivors of myocardial infarction. One study, which reports the relationship of levels of Lp(a) and coronary heart disease in patients who underwent coronary angiography, concluded that plasma Lp(a) appears to be a major independent risk factor for coronary heart disease. Elevation of plasma VLDL is seen in survivors of myocardial infarction, suggesting the possible involvement of this lipoprotein in the atheroschlerotic process.

Measurement of total cholesterol alone may not be adequate to identify subjects at risk for coronary heart disease. An individual with normal or near normal levels of total cholesterol may still be at risk because of low HDL levels, elevated Lp(a) levels, or elevated levels of VLDL. Moreover, the predictive power of total cholesterol for risk of coronary heart disease diminishes in men with increasing age. Therefore, assessment of the distribution of cholesterol among all the lipoproteins (a lipoprotein cholesterol profile), in addition to total cholesterol, is desirable in order to accurately assess risk for coronary heart disease.

Methods currently used to determine the concentration of cholesterol in the different lipoprotein classes can be divided into direct methods and indirect methods. In direct methods, lipoprotein cholesterol is determined by enzymatic assay of the individual lipoproteins, which are separated by ultracentrifugation, electrophoresis, or selective precipitation. The most accurate of these methods involves ultracentrifugation. However, ultracentrifugation separation methods are expensive, time-consuming, and are not practicable for clinical applications wherein multiple analyses are carried out in large numbers.

Another method of determination of cholesterol distribution among plasma lipoproteins involves the separation of lipoproteins by high performance liquid chromatography and the on-line detection of cholesterol in the postcolumn effluent using an enzymatic reagent. This method also provides a direct measure of lipoprotein cholesterol. However, this method requires a relatively long retention period of separation of the sample. Moreover, the separation technique results in some loss of lipoproteins which could result in an underestimation of cholesterol concentration.

Indirect methods, as a general rule, are better suited for clinical applications than are direct methods. The most commonly used method for measurements of lipoprotein cholesterol performs multiple analyses using different aliquots of the same plasma sample. Total cholesterol (TC) is measured using a first aliquot of the sample. In a second aliquot, VLDL and LDL are removed by precipitation and the supernatant is assayed for cholesterol to provide a measure of HDL cholesterol. An estimate of LDL is obtained by measuring the triglycerides (TG) in a third aliquot using the Friedewald formula or is measured directly after ultracentrifugal isolation of very low density lipoprotein. The LDL cholesterol concentration is not measured directly, but is calculated by subtracting the HDL cholesterol and VLDL cholesterol values from the total cholesterol.

Although this method is relatively rapid and inexpensive, there are several steps where error could be introduced. For example, accurate measurements of HDL depends on complete precipitation of apo-B containing lipoproteins. Traces of LDL in the supernatant can lead to overestimation of HDL cholesterol. Moreover, the multiple assumptions involved in the Friedewald formula make this method susceptible to error. In addition, this method does not provide a separate measure of IDL cholesterol or Lp(a) cholesterol. Instead, these values are included in the LDL cholesterol measurement.

The VAP method (Vertical Auto Profile) provides a direct method for determination of lipoprotein concentrations. The VAP method uses short spin density gradient vertical ultracentrifugation to separate the classes of lipoproteins. Analysis of cholesterol is made using an air segmented continuous flow analysis system to provide a lipoprotein cholesterol profile. The VAP method provides a direct measure of lipoprotein cholesterol using a single aliquot of plasma. However, VAP requires a relatively large sample (1.3 ml), and the equipment used in the VAP method is cumbersome, making its operation and maintenance difficult. Furthermore, this method causes overlapping of adjacent lipoprotein peaks in the cholesterol profile resulting in a substantial loss of resolution. Quantification of Lp(a) and IDL, which are not well-separated from other lipoproteins by density-gradient centrifugation becomes difficult particularly when present in small amounts.

An improvement of the original VAP method, known as the VAP II method, provides a direct method for determination of lipoprotein concentrations which is suitable for clinical applications. The VAP II method, like the VAP method, uses short spin density gradient vertical ultracentrifugation to separate the classes of lipoproteins. The separated sample is then introduced into a continuous flow analysis system to provide a profile of the cholesterol concentration in all lipoprotein classes. However, in contrast to the VAP method, the VAP II method continuously introduces the entire blood plasma sample into a non-segmented carrier stream while controlling dispersion of the sample. The VAP II method is described in U.S. Pat. No. 5,284,773, which is incorporated herein by reference. The VAP II method requires comparatively small samples of blood and is rapid enough to be used in large-scale population screening. However, the VAP II method in its current form requires highly skilled technicians to monitor the testing procedures, and requires human intervention at numerous points during the process.

Although low density lipoprotein (LDL) cholesterol is considered a primary risk factor, and hence the primary target for cholesterol-lowering therapy, there are several limitations of only using LDL cholesterol as the primary risk variable. In particular, this approach does not take into account atherogenicity of lipoprotein particles other than LDL. Several studies suggest that apolipoprotein $B_{100}$ (apo B), which is an integral part of all atherogenic particles and central to the lipoprotein transport system, is indeed far superior to LDL in predicting risk of coronary heart disease. This is because apo B is present in all atherogenic lipoprotein particles (i.e., LDL, Lp(a), IDL and VLDL), with each particle containing exactly one molecule of apo B. Thus, the measurement of apo B represents the total number of atherogenic particles. It is the apo B in the particles that leads to accumulation of these lipoproteins in the arterial wall which eventually leads to myocardial infarction (heart attack). In addition, apo B serves as a ligand for the apo B and apo B/E receptors thereby facilitating the uptake of cholesterol in peripheral tissues and the liver. Despite its high clinical importance, this important risk factor is not currently routinely measured in a clinical laboratory, primarily due to the additional cost involved. Currently, apo B is typically directly measured (using a specific apo B test method) which is reason for the additional cost and the reason that it is not routinely measured. It is desirable to provide a system and method that measures the concentration of apo B without requiring a separate apo B specific test and it is to this end that the system and method are directed.

DETAILED DESCRIPTION OF AN EXEMPLARY EMBODIMENT

The system and method are particularly applicable to the measurement of apo B in human blood and it is in this context that the system and method will be described. It will be appreciated, however, that the system and method has greater utility since it can be used to measure the apo B in other mammals and other liquids and the system is not limited to the measurement of apo B in human blood exemplary embodiment described below.

Figure 1:
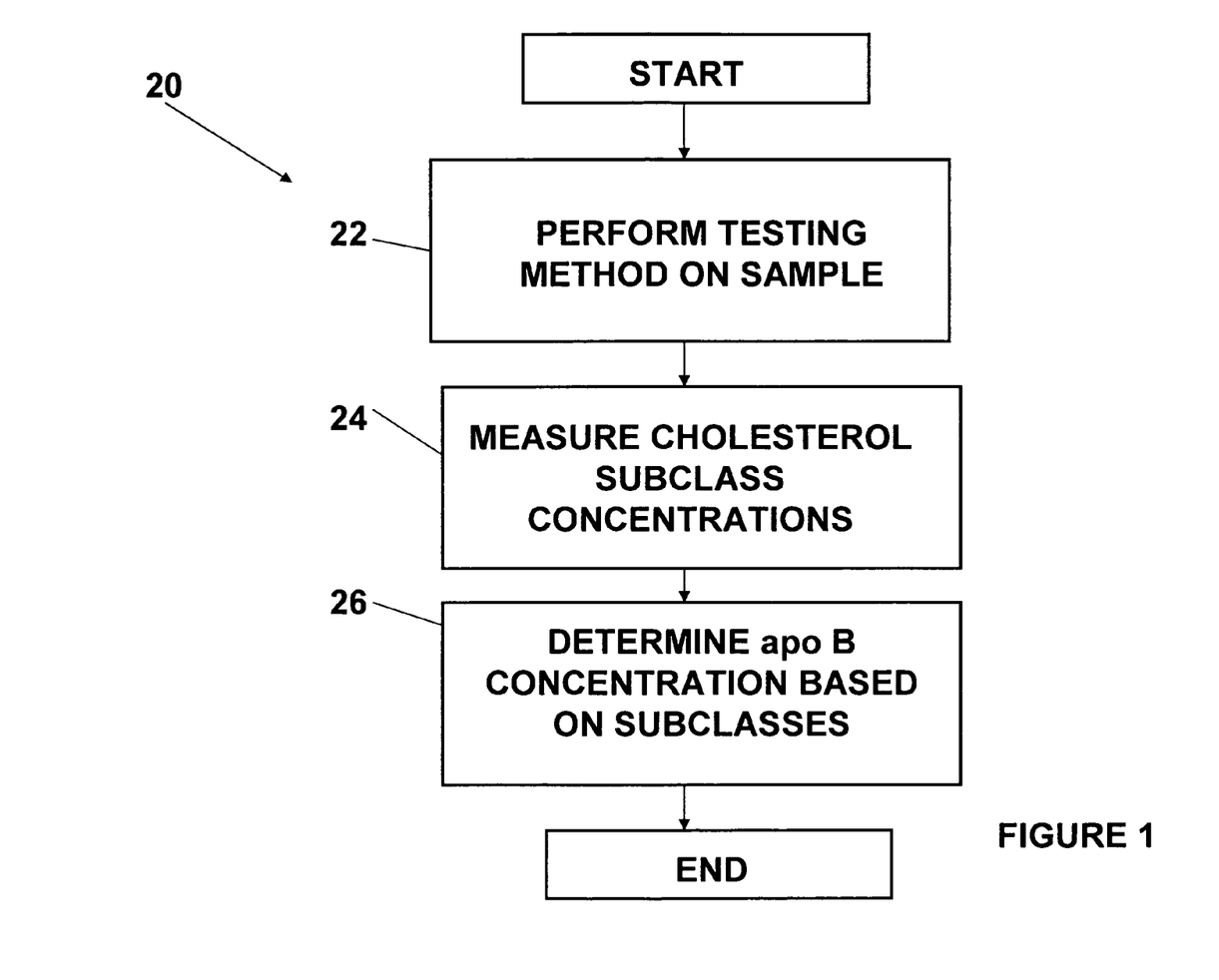
FIG. 1 illustrates a method for determining apolipoprotein $B_{100}$.

FIG. 1 illustrates a method 20 for determining apolipoprotein $B_{100}$ (apo B) wherein the apo B can be measured from the same values calculated during a cholesterol measurement/test so that the higher cost of a separate apo B test is not needed and more people will have access to the apo B test and the results of the measurement. A serum sample that is used for a cholesterol test is received and tested (22) to determine the various cholesterol subclasses (24) present in the sample. An exemplary process and device that can be used to measure the cholesterol subclasses in a sample known as the VAP test is described in more detail below as an example of a cholesterol subclass measurement process. The resulting cholesterol subclasses, such as low density lipoprotein (LDL), high density lipoprotein (HDL), intermediate density lipoprotein (IDL), lipoprotein (a) (Lp(a)) and/or very low density lipoprotein (VLDL), can then be used to provide a patient with cholesterol measurements that indicate a risk of heart disease or other diseases.

The resultant values of the cholesterol subclasses may then also be used to determine the apo B concentration in the serum (26) without re-testing the sample. In particular, it is known that each atherogenic lipoprotein (LDL-R, Lp(a), IDL and VLDL which are collectively known as non HDL-C) contains exactly one molecule of apo B. Thus, the measurements of the concentrators of these non HDL-C molecules can therefore be used to measure the level of apo B of a patient as described in more detail below. In an exemplary embodiment, the determination of the apo B concentration is performed by a piece of software having a plurality of lines of computer code wherein the plurality of lines of computer code are executed by a processing unit (such as a processing unit in a computer system) to determine the apo B concentration.

In order to determine the concentration of apo B, an initial formula to calculate apo B from non-HDL cholesterol subclasses was developed by analyzing the subclass concentrations (using the VAP test in the exemplary embodiment) for a predetermined number of patients and comparing it to directly measured apo B that was performed using a Architect/C8000 chemistry analyzer made by Abbott Diagnostics. To perform the above comparison, each week for five consecutive weeks, 105 specimens with 35 each of LDL pattern A, B, and A/B for a total of 525 subjects (called training set) were selected from patient specimens. The cholesterol subclass determinations were already performed on these specimens so that only apo B direct measurement was performed on the specimens. The results of the comparison are shown in Table 1 below.

TABLE 1

Linear regression results describing the relationship between VAP non HDL-Cholesterol ("non HDL-C") and directly measured apo B

| Week | Number of Subjects | Slope | Intercept | R |
|---|---|---|---|---|
| 1 | 105 | 0.542 | 22.3 | 0.961 |
| 2 | 105 | 0.553 | 20.3 | 0.961 |
| 3 | 105 | 0.546 | 19.1 | 0.944 |
| 4 | 105 | 0.545 | 23.0 | 0.942 |
| 5 | 105 | 0.573 | 18.2 | 0.971 |
| ALL | 525 | 0.5516 | 20.679 | 0.956 |

The initial study described above was performed over a period of five weeks in order to capture any long-term laboratory variation of the VAP test procedure and direct apo B analyses. The regression data in the above table suggest that the laboratory variation remained relatively constant each week. The initial formula for calculating apo B from VAP non HDL-C was determined to be (based on the results in Table 1):

VAP Calculated apo B=0.551614*non-HDL-C+20.67944

Figure 2:
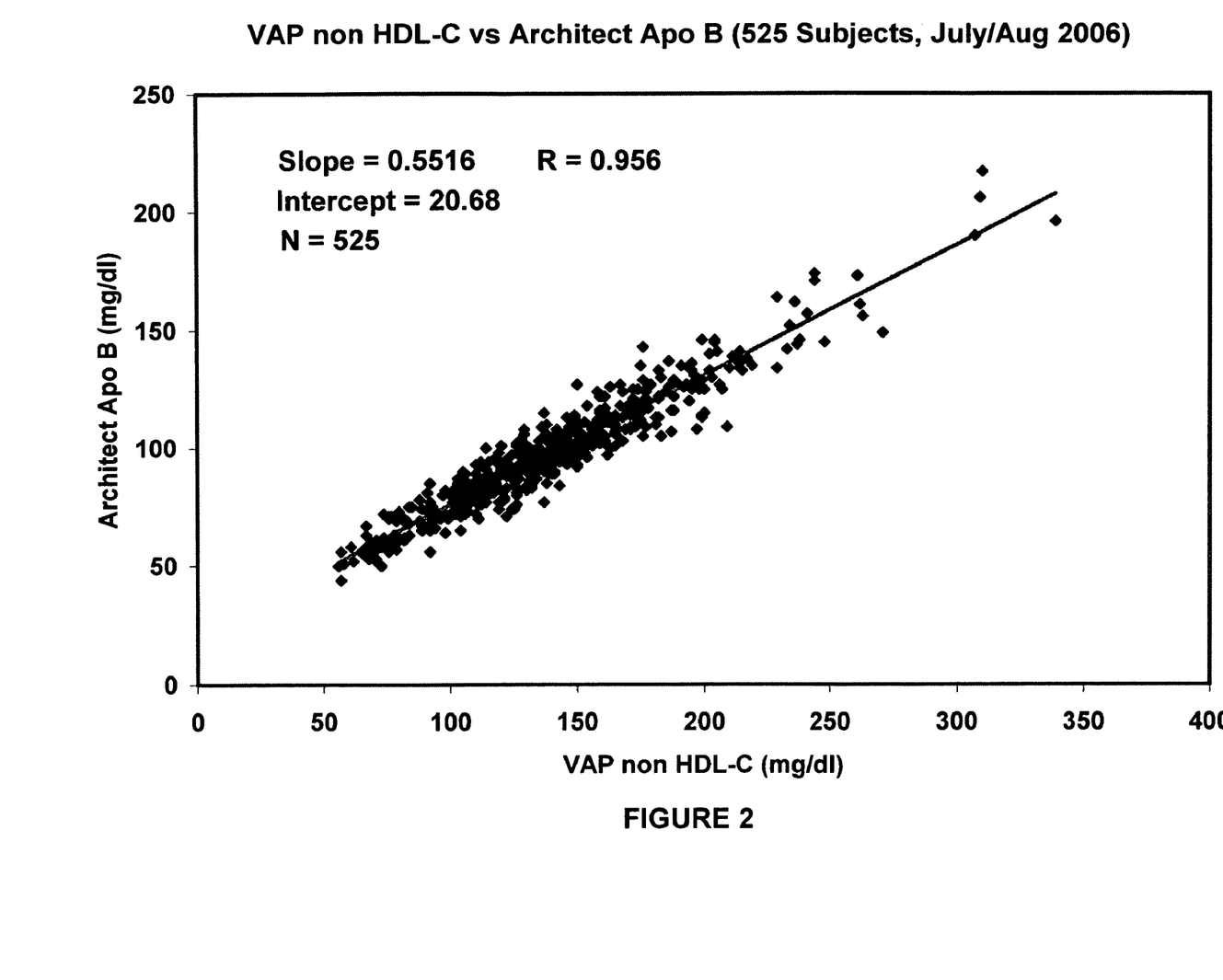
FIGS. 2, 3 and 4 are plots illustrating the relationship between apolipoprotein $B_{100}$ and non-HDL and determined apolipoprotein $B_{100}$ compared to measured apolipoprotein $B_{100}$, respectively.

FIG. 2 is a scatter plot showing the linear relationship between the measured apo B and VAP non HDL-C using all 525 subjects described above.

The above formula was then tested and validated on two different days, each time using 100 freshly received patient specimens (test sets 1 and 2). The non HDL-C and other lipoproteins were measured using the VAP test as before and apo B was measured on all samples using two different Architect/C8000 chemistry analyzer made by Abbott Diagnostics. The VAP apo B then was calculated for each sample using the above described formula. The VAP calculated apo B was then compared with the measured apo B for individual test sets and individual Architect/C8000 units as well as combined data (i.e., from both test sets and both Architect/C8000 units, thus N=400) using linear regression analysis. The results of these analyses are shown in Table 2 below.

TABLE 2

Comparison of VAP calculated Apo B with measured Apo B using 200 subjects

|  | Test Set 1/ Architect 12607 (N = 100) | Test Set 1/ Architect 12611 (N = 100) | Test Set 2/ Architect 12607 (N = 100) | Test Set 2/ Architect 12611 (N = 100) | Both Sets/Both Architects (N = 400) |
|---|---|---|---|---|---|
| Measured Apo B Mean ± SD (mg/dl) | 94.0 ± 21.5 | 90.4 ± 21.6 | 95.5 ± 29.3 | 95.0 ± 29.7 | 93.7 ± 25.8 |
| VAP Calculated Apo B Mean ± SD (mg/dl) | 97.9 ± 21.1 | 97.9 ± 21.1 | 101.7± 27.7 | 101.7 ± 27.7 | 99.8 ± 24.6 |
| % Difference (Calc – Meas) | 4.1% | 8.3% | 6.5% | 7.1% | 6.5% |
| Slope | 0.924 | 0.915 | 0.906 | 0.893 | 0.905 |
| Intercept | 11.0 | 15.1 | 15.2 | 16.9 | 14.9 |
| R | 0.941 | 0.936 | 0.960 | 0.956 | 0.950 |

Although the above comparison between VAP calculated apo B and measured apo B using linear regression analysis appears satisfactory, the results were further compared by determining the percentage difference between individual subject's VAP calculated apo B and measured apo B (i.e., percentage bias) for the combined data (last column in the above table). These percentage differences were used to determine the percentage of total patients who had the difference between calculated and measured apo B within defined ±bias ranges. The results from this analysis are shown in Table 3 below.

TABLE 3

Percent of patient population whose VAP calculated Apo B is within a given ± percent bias range of measured Apo B

| Bias range of (Cal. – Meas.) Apo B | Number of Patients (of the 400 from Test Sets 1 + 2/Architects 1 + 2) | % of patients |
|---|---|---|
| ±5% | 141 | 35% |
| ±10% | 255 | 64% |
| ±15% | 327 | 82% |
| ±20% | 374 | 94% |
| ±(20% to 30%) | 21 | 5% |
| >±30% | 6 | 1.5% |

The data in Table 3 shows that if this formula for calculating apo B from VAP non HDL-C is implemented, 64% of the tested patients are likely to have calculated apo B within ±10% of the directly measured value, and 94% within ±20% of the measured value. In an alternative embodiment of the process, it is desirable to increase the percentage of patients with calculated value within ±10% of measured value by improving the accuracy of the process. A modification of the above apo B determination in the alternative embodiment based on scientific knowledge and experimental work that incorporates the LDL pattern information into the apo B determination is described in more detail below. In the alternative embodiment, the level of triglycerides (TG) in the sample of the patient affects the apo B determination and the influence of the triglycerides (TG) level on the apo B determination is now described before describing the alternative embodiment of the apo B determination.

Influence of Triglyceride Concentration on Apo B Calculation

As described earlier, the formula to calculate apo B from VAP non HDL-C assumes a constant ratio of cholesterol to apo B in each non HDL particle. However, it is known that this ratio decreases as triglycerides concentration increases substantially. In addition, the number of specimens with increasing chylomicrons (lipemic specimen) or their remnants increases as triglyceride levels increase. Since chylomicrons and their remnants do not possess apo $B_{100}$ (they instead have apo $B_{48}$ which is a truncated form of apo $B_{100}$, not measured by the Architect/C8000 device) a significant positive bias is likely with increasing serum TG (particularly for TG>500). Since neither the training set nor the test sets described above contained a significant number of specimens with elevated TG (>500 mg/dl), the influence of TG was independently determined by performing apo B analysis on selected sets of specimens whose triglycerides measured by Architect/C8000 ranged from 300 to at least 1,000 mg/dl.

Apo B was calculated using the above formula for all specimens used to study the influence of TG. The results obtained from comparing calculated with measured apo B are shown in Table 4 in which two different chemical analysis devices (Architect/C8000 S. No. 12607 and Architect/C8000 S. No. 12611) are used.

TABLE 4

Comparison of VAP calculated apo B with measured apo B using specimens with different levels of TG (for the purpose of comparison results from Test Sets 1 and 2 are also shown).

Architect/C8000 S. No. 12607:

| | | | | | C8000#12607 | | |
|---|---|---|---|---|---|---|---|
| Specimens (TG Range) | N | Slope | Intercept | R | Mean (SD) Meas. Apo B | Mean (SD) Calc. ApoB | % Difference |
| Test Set1 (Any TG) | 100 | 0.924 | 11.0 | 0.941 | 94.0 (21.5) | 97.9 (21.1) | 4.1 |

TABLE 4-continued

Comparison of VAP calculated apo B with measured apo B using specimens with different levels of TG (for the purpose of comparison results from Test Sets 1 and 2 are also shown).

| | N | Slope | Intercept | R | Mean (SD) Meas. ApoB | Mean (SD) Calc. ApoB | % Difference |
|---|---|---|---|---|---|---|---|
| Test Set 2 (Any TG) | 100 | 0.906 | 15.2 | 0.959 | 95.5 (29.3) | 101.7 (27.7) | 6.5 |
| Test Set1 + 2 (Any TG) | N = 400 | 0.905 | 14.9 | 0.950 | 93.7 (25.8) | 99.8 (24.6) | 6.5 |
| Test Set 3 (TG 300-400) | 51 | 0.881 | 17.5 | 0.923 | 111.6 (23.6) | 115.8 (22.5) | 3.8 |
| Test Set 4 (TG 400-500) | 49 | 0.859 | 21.5 | 0.871 | 119.9 (27.8) | 124.6 (27.4) | 3.9 |
| Test Set 5 (TG 500-600) | 35 | 1.03 | 0.6 | 0.819 | 122.8 (32.0) | 127.3 (40.3) | 3.7 |
| Test Set 6 (TG 600-700) | 35 | 0.758 | 34.5 | 0.891 | 124.8 (32.7) | 129.1 (27.8) | 3.4 |
| Test Set 7 (TG 700-800) | 26 | 0.800 | 33.2 | 0.782 | 120.8 (29.6) | 129.5 (30.2) | 7.2 |
| Test Set 8 (TG 800-900) | 14 | 0.702 | 47.4 | 0.735 | 123.1 (32.0) | 133.8 (30.5) | 8.7 |
| Test Set 9 (TG 500-1000) | 65 | 0.822 | 28.0 | 0.889 | 124.7 (35.3) | 130.6 (32.6) | 4.7 |

Architect/C8000 S. No. 12611:

| Specimens (Trigs Range) | N | Slope | Intercept | R | Mean (SD) Meas. ApoB | Mean (SD) Calc. ApoB | % Difference |
|---|---|---|---|---|---|---|---|
| Test Set1 (Any TG) | 100 | 0.915 | 15.1 | 0.936 | 90.4 (21.6) | 97.9 (21.1) | 8.3 |
| Test Set 2 (Any TG) | 100 | 0.893 | 16.9 | 0.956 | 95.0 (29.7) | 101.7 (27.7) | 6.7 |
| Test Set1 + 2 (Any TG) | N = 400 | As in above Table | | | | | |
| Test Set 3 (TG 300-400) | 51 | 0.876 | 18.1 | 0.925 | 111.6 (23.8) | 115.8 (22.5) | 3.8 |
| Test Set 4 (TG 400-500) | 49 | 0.872 | 19.0 | 0.879 | 120.9 (27.6) | 124.6 (27.4) | 3.1 |
| Test Set 5 (TG 500-600) | 35 | 1.01 | 2.9 | 0.815 | 122.7 (32.4) | 127.3 (40.3) | 3.7 |
| Test Set 6 (TG 600-700) | 35 | 0.750 | 37.5 | 0.890 | 122.1 (33.0) | 129.1 (27.8) | 5.7 |
| Test Set 7 (TG 700-800) | 26 | 0.762 | 36.6 | 0.769 | 121.8 (30.5) | 129.5 (30.2) | 6.3 |
| Test Set 8 (TG 800-900) | 14 | 0.696 | 50.3 | 0.744 | 120.1 (32.6) | 133.8 (30.5) | 11.4 |
| Test Set 9 (TG 500-1000) | 65 | 0.765 | 31.0 | 0.898 | 130.2 (38.3) | 130.6 (32.6) | 0.3 |

The above results suggest that for specimen sets with TG>500, either correlation coefficient or slope/intercept were not favorable. This might be caused by increasing number of specimens with chylomicrons when TG increases. In an exemplary embodiment, the apo B determination in the alternative embodiment is not used for patients who has TG>499 which may be up to 2% of the patients.

Alternative Embodiment Apo B Determination

As discussed previously, one of the limitations of the above formula for apo B calculation is its assumption that cholesterol to apo B ratio remains constant for all types of atherogenic particles. This, however, leads to an overestimation of calculated apo B for specimens with predominantly large and buoyant LDL, which are rich in cholesterol (LDL pattern A) and an underestimation for specimens with predominantly small and dense LDL, which are depleted of cholesterol (LDL pattern B). Therefore, in the alternative embodiment, the apo B determination uses separate formulas for each LDL pattern group. In order to test this alternative embodiment, the data obtained using 525 subjects (training set) above was recalculated by grouping the patients into three groups based upon their LDL pattern, i.e., LDL pattern A group, LDL pattern B group, and LDL pattern A/B group.

LDL particles are heterogeneous with respect to their physical and chemical properties, including hydrated density, particle size and shape and chemical composition. Several subclasses of LDL with differing physico-chemical properties have been shown to exist by various techniques such as gradient gel electrophoresis and density gradient ultracentrifugation in hypertriglyceridemic patients as well as normal subjects. A characteristic of LDL subclass distributions (LDL phenotype) that has yielded clinical relevance is predominance of smaller, more dense (designated as LDL pattern B) versus larger, more buoyant LDL particles (designated as LDL pattern A) in serum. Thus, when a serum from a patient with LDL pattern B is analyzed by 2-16% gradient gel electrophoresis (GGE), the major peak usually appears with a peak size <255 Å (angstrom) while a minor peak appears with a peak size >255 Å. On the other hand, when a serum from a patient with LDL A is analyzed by 2-16% gradient gel electrophoresis (GGE), the major peak usually appears with a peak size >255 Å while a minor peak appears with a peak size <255 Å. A small percentage of patients are characterized by intermediate or double-peak pattern and therefore they are classified as LDL pattern A/B. Since the separation of lipoproteins and their subclasses by the VAP method depends upon their density and the density of lipoprotein is inversely proportional to the size of lipoprotein LDL floats to a lesser extent in the centrifuge tube in a patient with LDL pattern B (predominance of small, more dense LDL) compared to the patient with LDL pattern A (predominance of large, more buoyant LDL). Thus, the relative position of the LDL peak maximum in the VAP profile (See FIG. 7) in patients with LDL pattern B is more towards the bottom of the centrifuge tube (beginning of the profile because contents of the tube are drained from the bottom) compared to the LDL peak maximum of patients with LDL pattern A. There has been increasing interest in LDL subclass patterns recently due to the finding from several studies that small, dense LDL (LDL pattern B) is more prevalent in patients with coronary heart disease.

Thus, in the alternative embodiment, a separate formula describing the relationship between non HDL-cholesterol and apo B was derived for each group by linear regression analysis, similar to the above formula developed for using all 525 subjects. The relationship between non HDL-C and measured apo B for each group was linear and highly correlated. However, as expected, the slope and intercept for each group were somewhat different, which indeed to some extent account for the differences in cholesterol to apo B composition in these groups.

The following apo B determination formulas were derived for each group.

For Patients with LDL Pattern A (TG<500): VAP Calculated Apo B=0.548939*non HDL-Cholesterol+17.50609

For Patients with LDL Pattern B (TG<500): VAP Calculated Apo B=0.55694*non HDL-Cholesterol+24.11059

For Patients with LDL Pattern A/B (TG<500): VAP Calculated Apo B=0.55809*non HDL-Cholesterol+19.72473

Figure 3:
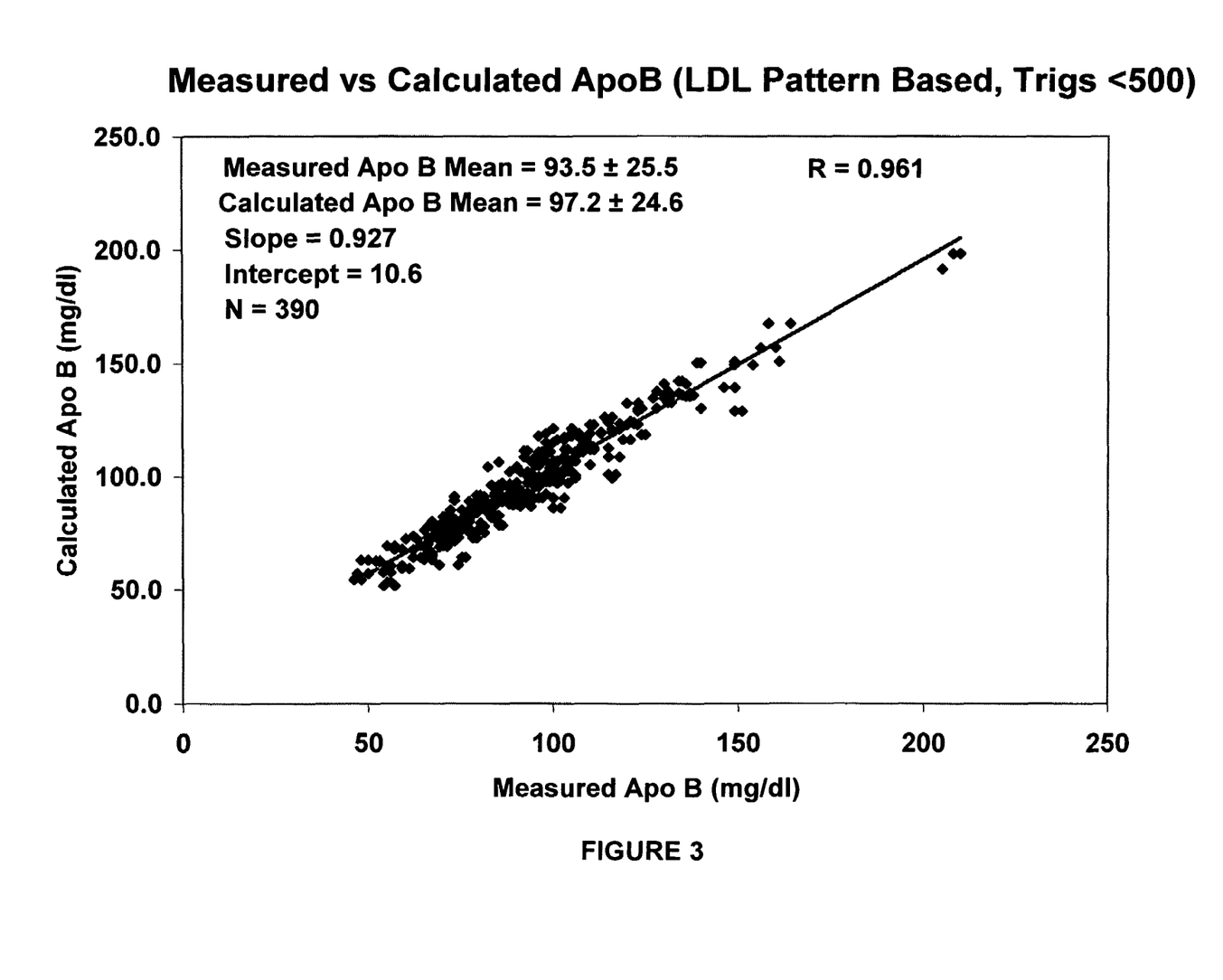

The above apo B determination formulas were tested using the same data from Test Set 1 and Test Set 2 performed using both Architects (N=390, as 5 patients with TG>500 were excluded). The VAP calculated apo B were compared with the measured apo B and the results obtained are shown in FIG. 3. As shown in FIG. 3, the results suggest an excellent agreement between VAP calculated apo B and directly measured apo B, with only a 4.0% mean difference (bias) between the two values (calculated values being higher). In addition, as before, the percentage of total number of patients who had the percentage bias within defined percentage bias ranges was also determined. The results from this analysis are shown in Table 5 below.

TABLE 5

Percent of patient population whose VAP calculated Apo B is within a given ± percent of measured Apo B

| Bias range of (Cal. − Meas. Apo B) | Number of Patients (of the 390 from Test Sets 1 + 2/Architects 1 + 2, TG < 500) | % of patients |
| --- | --- | --- |
| ±5% | 96 | 48% |
| ±10% | 149 | 74.5% |
| ±15% | 179 | 89.5% |
| ±20% | 191 | 95.5% |
| >±20% | 9 | 4.4% |

Comparison of results from initial and modified apo B calculation formulas shown in Table 6 below clearly suggest an improvement in accuracy with modified formula based upon LDL pattern information.

TABLE 6

Comparison of results from combined test sets 1 and 2 obtained using initial (VAP non HDL-C based) and modified (VAP non HDL-C and LDL pattern based) apo B calculation formulas

| Parameter | Initial (VAP non HDL-C based) apo B formula | Modified (VAP non HDL-C and LDL pattern based) apo B formula |
| --- | --- | --- |
| Correlation Coefficient | 0.950 | 0.961 |
| Slope | 0.905 | 0.927 |
| Intercept | 14.9 | 10.6 |
| % bias between the calculated and measured mean values | 6.5% | 4.0% |
| % of patients with calculated apo B within ±5% of measured apo B | 35% | 48% |
| % of patients with calculated apo B within ±10% of measured apo B | 64% | 74.5% |
| % of patients with calculated apo B within ±15% of measured apo B | 82% | 89.5% |
| % of patients with calculated apo B within ±20% of measured apo B | 94% | 95.5% |

The above apo B determination were validated by laboratory operations in which VAP tests were run and apo B was directly measured on at least 200 freshly received patient specimens each day, for six days. The total number of specimens tested was 1264 over a six day period. The LIS calculated VAP apo B values were compared with the directly measured apo B values by both linear regression analysis and determining the percent bias between calculated and measured values for each patient. The results obtained by regression analysis on individual days and from all six days combined are shown in Table 7.

TABLE 7

Comparison of VAP calculated apo B and directly measured apo B using linear regression analysis by the laboratory operations

| Day | N | Slope | Intercept | R | Mean Measured Apo B | Mean Calculated Apo B | % Bias |
| --- | --- | --- | --- | --- | --- | --- | --- |
| 1 | 200 | 0.88 | 15.3 | 0.962 | 98.6 ± 24.9 | 102.1 ± 22.8 | 3.5% |
| 2 | 201 | 0.91 | 12.5 | 0.967 | 93.0 ± 28.3 | 97.5 ± 26.7 | 4.8% |
| 3 | 216 | 0.90 | 11.4 | 0.964 | 93.3 ± 24.5 | 95.6 ± 23.0 | 2.5% |
| 4 | 216 | 0.87 | 18.3 | 0.958 | 94.0 ± 25.5 | 99.6 ± 23.1 | 6.0% |
| 5 | 216 | 0.92 | 11.3 | 0.965 | 95.3 ± 27.4 | 98.9 ± 26.1 | 3.8% |
| 6 | 216 | 0.90 | 10.7 | 0.958 | 92.6 ± 25.4 | 93.8 ± 23.7 | 1.3% |
| All days | 1264 | 0.90 | 13.0 | 0.961 | 94.4 ± 26.1 | 97.9 ± 24.4 | 3.6% |

Figure 4:
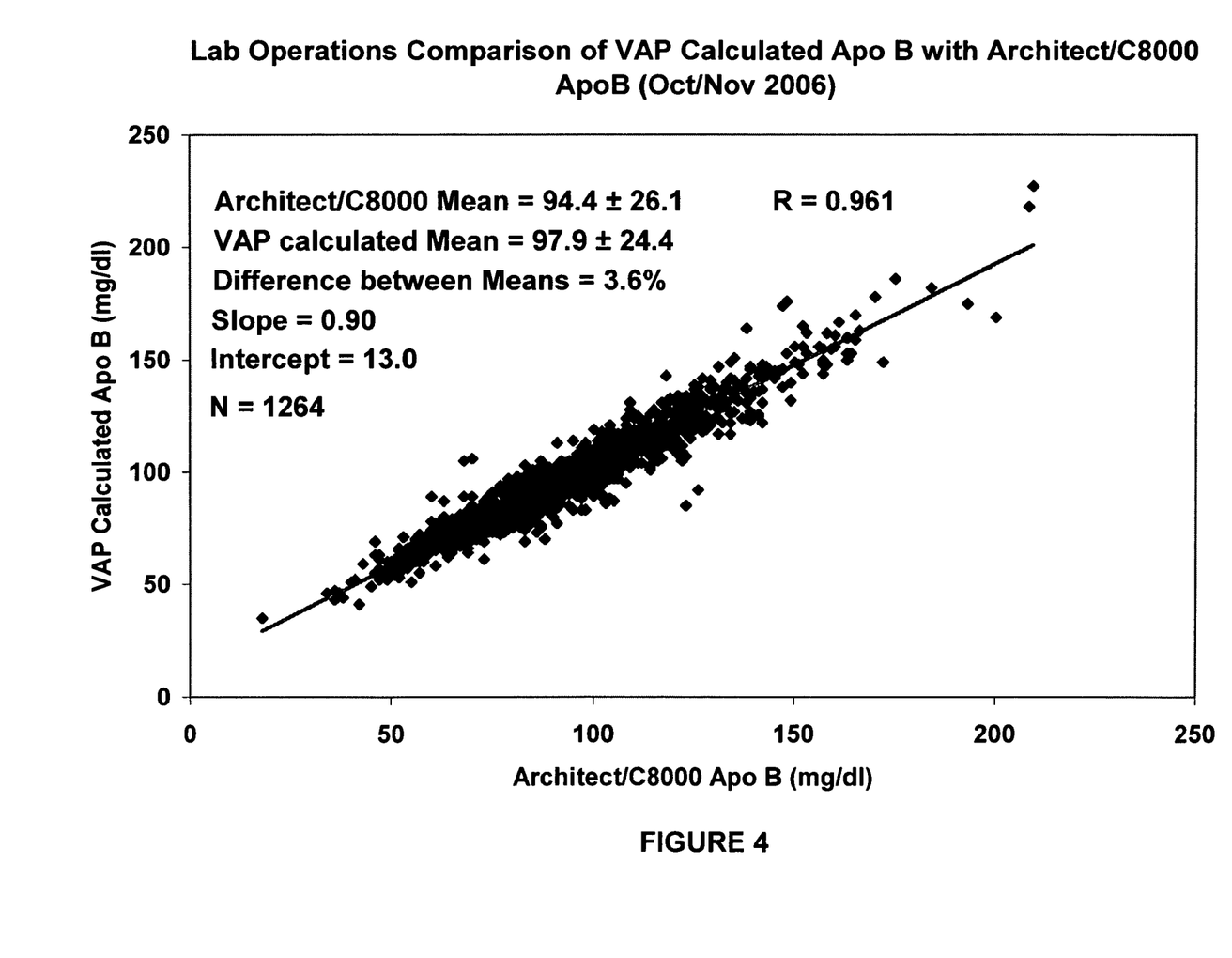

The scatter plot showing the relationship between VAP calculated apo B (LIS reported) and directly measured apo B from all subjects (i.e., from all days combined, N=1264) is shown in FIG. 4. In addition, as before, percent of patients with a given % bias range between VAP calculated apo B and measured apo B were calculated for individual days and combined days. The results obtained are shown in Table 8.

TABLE 8

Percent of laboratory operations tested patient population whose VAP calculated Apo B is within a given ± percent of measured Apo B

|  | Percent of patients with ±5% Bias between cal. and meas. apo B | Percent of patients with ±10% Bias between cal. and meas. apo B | Percent of patients with ±15% Bias between cal. and meas. apo B | Percent of patients with ±20% Bias between cal. and meas. apo B |
|---|---|---|---|---|
| Day 1 | 48.5% | 74.5% | 91.0% | 95.5% |
| Day 2 | 41.3% | 71.1% | 83.6% | 93.0% |
| Day 3 | 49.1% | 81.5% | 93.5% | 97.7% |
| Day 4 | 38.9% | 65.7% | 81.5% | 90.7% |
| Day 5 | 50.0% | 74.1% | 85.6% | 93.5% |
| Day 6 | 48.8% | 79.1% | 92.1% | 98.1% |
| All Days | 46.1% | 74.4% | 87.9% | 94.9% |

The above results obtained from a large and rigorous validation by the lab operations are in excellent agreement with the results obtained from the testing of the formulas done during the development work (Compare FIG. 3 vs FIG. 4, Table 5 vs Table 8, and Table 6 vs Table 7).

Figure 5:
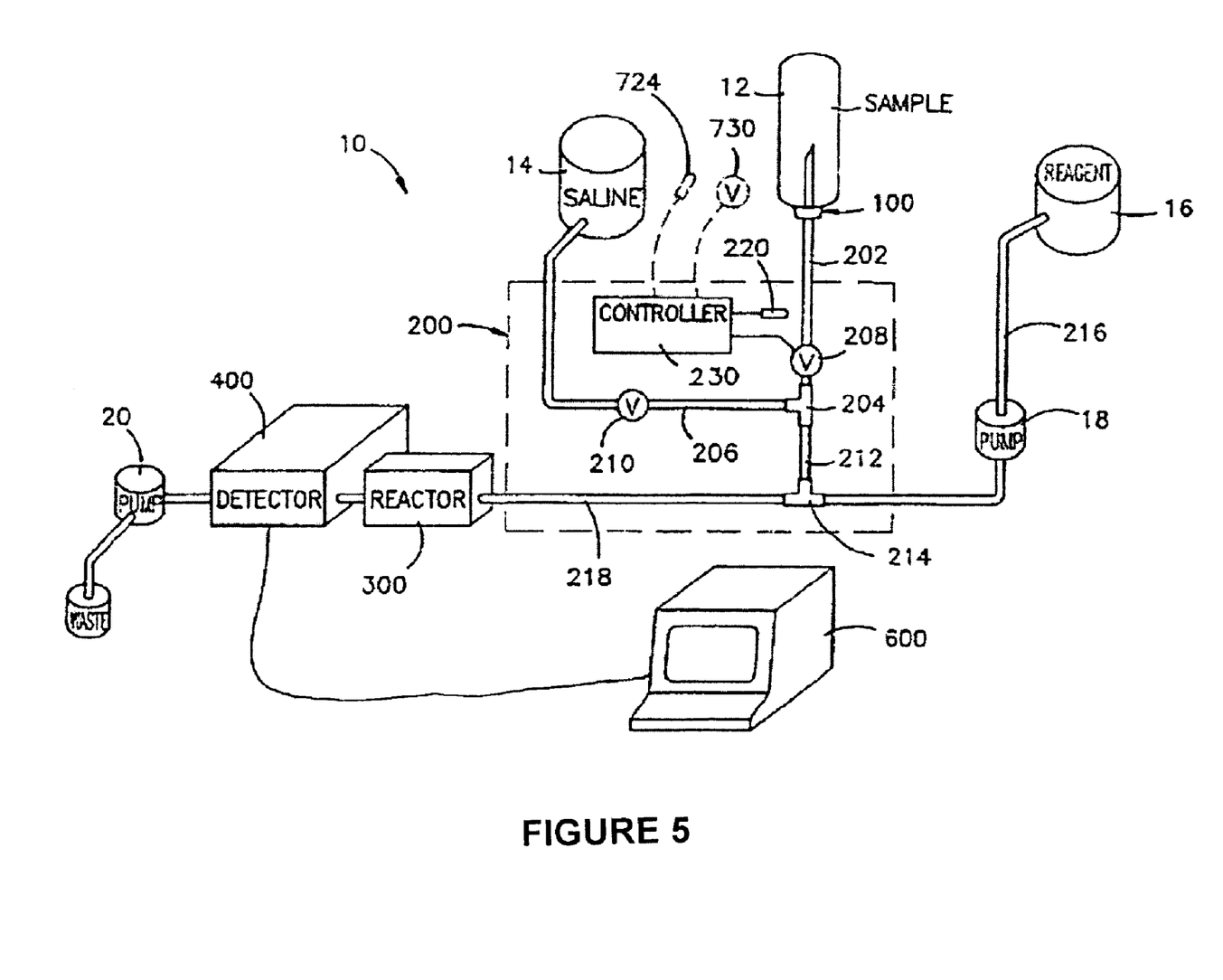
FIG. 5 is a schematic illustration of the controlled dispersion flow analysis system that may be used as part of the method shown in FIG. 1.
Figure 7:
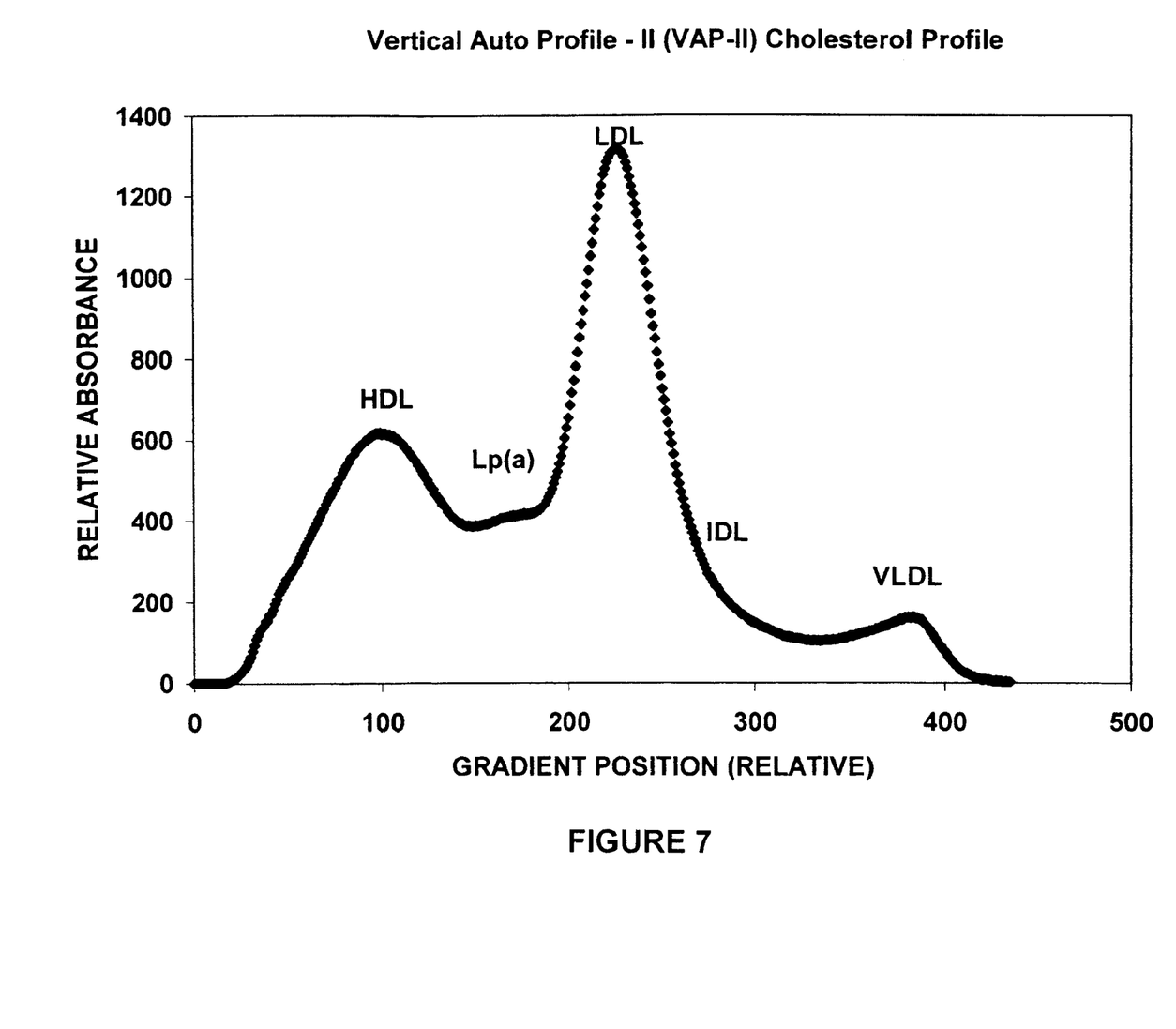
FIG. 7 is a typical cholesterol profile produced using the system shown in FIG. 5.

Now, an example of a testing system and method that can be used to determine the cholesterol subclasses of a patient sample is described. FIG. 5 is a schematic illustration of a controlled dispersion flow analysis system which is indicated generally by the numeral 10. FIG. 7 illustrates an example of a vertical auto profile (VAP-II profile) that shows the different subclasses of cholesterol such as the HDL, Lp(a), LDL, IDL and VLDL subclasses. The controlled dispersion flow analysis system 10 includes a tube-piercing needle assembly 100 for piercing a sample tube containing a blood serum sample which has been separated into individual lipoprotein classes by ultracentrifugation; a flow control sub-system 200 for mixing the sample with a continuous, non-segmented reagent stream; a reaction unit 300 for reacting the sample with the reagent to produce a reaction signal indicative of the cholesterol concentration in the sample; a detector 400 for monitoring the reaction signal; and a computer 600 for recording of the cholesterol profile and for collecting and analyzing absorbance data.

The needle assembly 100 is used to puncture a sample tube 12 and to feed the sample to the flow control sub-system 200. The needle assembly 100 can be any commercially available flow through needle. A saline reservoir 14 and reagent reservoir 16 are also connected to the flow control sub-system 200. A piston pump 18 provides a continuous, non-segmented stream of reagent to the flow control subsystem 200 throughout the test cycle. A second piston pump 20 is disposed upstream of the detector 400. The second piston pump 20 is operated at a higher rate than the first piston pump 18 to induce the saline solution and sample into the flow control sub-system 200.

During operation, the flow control sub-system 200 selectively controls the flow of saline solution and sample. Initially, saline solution is allowed to flow through the flow control sub-system 200 to mix with the reagent. The saline solution is used to establish a baseline. After a predetermined period of time, the flow of saline solution is stopped and the sample is fed into the flow control sub-system 200. The sample mixes with the reagent and flows through the reaction unit 300 and then to the detector 400 which measures a characteristic of the reaction mixture to determine the cholesterol concentration in the sample.

The flow control sub-system 200 includes a sample supply line 202 which connects the needle assembly 100 to one input of a Y-connector 204. The Y-connector 204 has two inputs and one output. The opposing input of the Y-connector 204 is connected by a supply line 206 to the saline reservoir 14. Supply line 202 passes through a first pinch valve 208 used to selectively start and stop the flow of fluid from the sample tube. A second pinch valve 210 is used to selectively start and stop the flow of saline solution from reservoir 14. The outlet of the Y-connector 204 is connected by an outlet line 212 to a second Y-connector 214. Connector 214 also includes two inputs and one output. Also connected to the Y-connector 214 is a reagent supply line 216 for supplying a continuous, non-segmented stream of reagent. The outlet of the connector 214 is connected by a reaction tube 218 to the reaction unit 300. From the reaction unit 300, the fluid flows through a detector 400 which measures the absorbance of the mixture passing through the detector 400. The absorbance in the form of a graph is also monitored on the computer screen during sample analysis.

The flow control sub-system 200 is controlled by an electrical controller 230. The electrical controller 230 may be either a programmable controller or an equivalent hard-wired electrical circuit. The electrical controller receives input from a sensor 220 which detects the end of the sample as it enters the flow control sub-system 200. The outputs of the electrical controller are used to control the pinch valves 208 and 210.

During an analysis, reagent flows continuously through the flow control subsystem 200. The serum sample and saline solution are delivered at selected points in the analysis. The flow control sub-system 200 allows automatic switching between delivery of sample and saline solution at appropriate times in the analysis. The reaction unit is a water bath maintained at 40 degrees C. with reaction tube 218 immersed in the water bath in the form of a coil.

The detector 400 is disposed downstream from the reaction unit 300. The detector 400 comprises a spectrophotometer which measures the absorbance of the reaction mixture as it passes through the detector 400. The absorbance is measured at 505 nm. The reaction signal measured by the detector 400 produces a cholesterol profile which is monitored dynamically by the computer 600 which also collects the absorbance data. A typical absorbance curve or cholesterol profile is illustrated in FIG. 7. Each point on the absorbance curve corresponds to the concentration of cholesterol in the blood plasma sample. The cholesterol profile is deconvoluted by the computer 600 to determine the cholesterol concentration associated with each class of lipoproteins.

Figure 6:
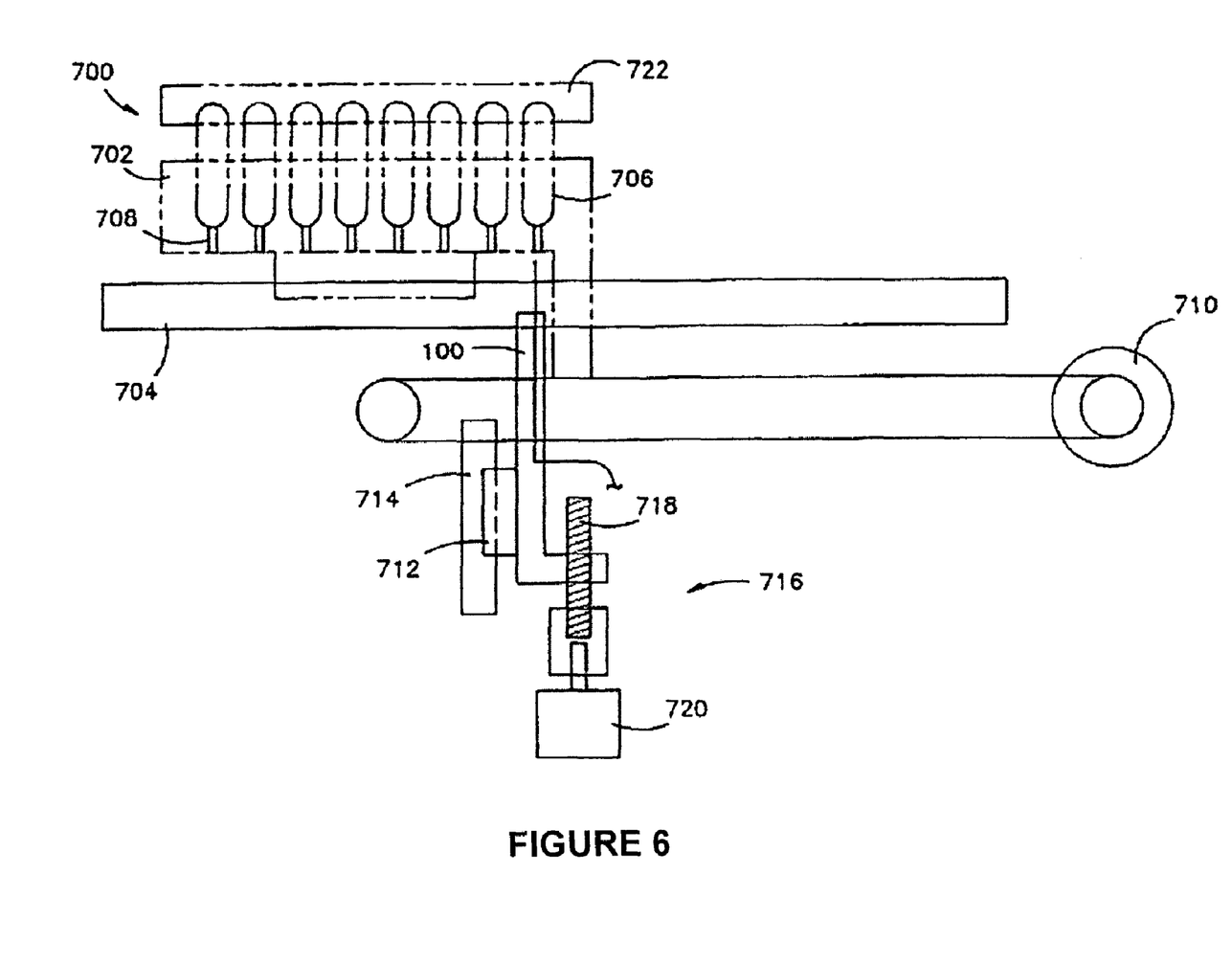
FIG. 6 is an elevation view of a first embodiment of the tube positioning and puncturing assembly of the system shown in FIG. 5.

The controlled dispersion flow apparatus 10 may also include an automatic tube positioning and puncturing assembly 700. FIG. 6 shows one embodiment of a tube positioning and puncturing assembly to allow for more automated sampling. As shown in FIG. 6, a tube fixture 702 is slidably mounted on a linear bearing track 704. The tube fixture 702 includes a plurality of tube wells 706 for receiving sample tubes containing the blood serum samples. A needle hole 708 extends from the bottom of the tube fixture 702 to each of the tube wells 706.

The tube fixture 702 is driven by a stepper motor 710 to position the sample tubes with respect to the needle assembly 100. The needle assembly 100 is mounted on a carriage 712 which slides vertically along a second linear bearing track 714. The carriage 712 is driven by a ball drive mechanism 716 including a ball screw 718 and stepper motor 720 to move the needle assembly 100 between an extended position and a retracted position.

In operation, the stepper motor 720 positions the tube fixture 702 such that the first tube is aligned with the needle assembly 100. A sensor 724 (See FIG. 5) checks to determine if a tube is present in the fixture 702, and, if so, the ball drive mechanism 716 is actuated to extend the needle assembly 100. As the needle assembly 100 is extended, it passes through the needle hole 708 in the tube fixture 702 and punctures the sample tube. A hold-down cap 722 holds the sample tubes down as the tubes are punctured by the needle assembly 100. The flow control sub-system 200 will then begin its automatic sequence as described below. In a preferred embodiment of the invention, the programmable controller is responsive to the signal from sensor 724 to close valve 210 and open valve 208 to start the flow of the blood sample. When the cycle is complete, the tube fixture 702 is indexed and the process is repeated until all samples have been tested.

Prior to analysis of the serum samples, the cholesterol reagent (Cholesterol/np, Roche Diagnostics) is placed in the reagent reservoir 16. All liquid solutions, including cholesterol reagent solution, are degassed by laboratory vacuum to minimize air bubble formation.

The serum sample is diluted with a 1.21 kg/l KBr solution. A discontinuous gradient is formed in a 5 ml ultracentrifuge tube by first pipetting the saline/EDTA solution (0.9% NaCl, 1 mmol/EDTA, ph=7.4 and density=1.006 kg/l) into each tube and then underlaying with density adjusted serum. The tubes are then sealed and placed in a rotor and centrifuged. After centrifugation, the tube is punctured by the needle assembly 100 at the bottom so as not to disturb the formed gradient.

The first stage of the testing process is referred to herein as the baseline stage. During the baseline stage, pinch valve 208 is closed and pinch valve 210 is opened to permit the flow of saline solution through the flow control sub-system 200. The saline solution is mixed with the reagent, which flows continuously through the process, at the Y-connector 214. The saline solution and reagent are blended as they flow through the reaction unit 300 and detector 400. The saline solution provides a baseline against which the cholesterol values are compared. Saline solution is used to establish a baseline because it has a density which closely matches the density at the bottom of the sample gradient and thus avoids any artifact at the baseline due to change in the absorbance caused by change in density of the sample.

At the completion of the baseline stage, pinch valve 208 is opened while pinch valve 210 is simultaneously closed to start the sample drain and stop the flow of saline solution into the flow control sub-system 200. This begins the sample testing phase during which the blood sample flows through the flow control sub-system 200 and continuously mixes with the reagent at connector 214. The sample and reagent form a reaction mixture as it moves through the reaction unit 300. After exiting the reaction unit 300, the reaction mixture flows through the spectrophotometer 400 which measures the absorbance of the reaction mixture at 505 nm. The computer 600 records the absorbance measured by the detector 400 in the form of a graph to produce a cholesterol profile and also stores and analyzes the absorbance data. The computer deconvolutes the absorbance data to make a quantitative determination of cholesterol in the individual lipoprotein classes.

A meniscus detector 220 senses the end of the sample as the sample drains into the flow control sub-system 200. When the end of the sample is sensed by the meniscus detector 220, ending the sample testing phase, the pinch valve 210 is opened to start the flow of saline solution into the flow control sub-system to begin the cleaning stage. While both valves 208 and. 210 are opened, saline solution backflows through the supply line 202 to flush any air bubbles or residue back into the sample container. To ensure that the saline solution backflows through the sample supply line 202, the saline reservoir 14 can be positioned at a height above the sample container sufficient to create pressure that will cause the saline solution to back flow through supply line 202. When the predetermined time delay elapses, pinch valve 208 closes while valve 210 remains open. Thus, saline solution continues to flow to reestablish the baseline for the next sample.

The controlled dispersion flow analysis system of the present invention provides a reliable method for controlling the flow of fluids during a test procedure. Once the test procedure is initiated, any further human intervention is avoided. Further, compared studies showed that the test results produced in accordance with the present invention are highly correlated with other procedures currently in use in clinical applications.

While the foregoing has been with reference to a particular embodiment of the invention, it will be appreciated by those skilled in the art that changes in this embodiment may be made without departing from the principles and spirit of the invention, the scope of which is defined by the appended claims.

The invention claimed is:

1. A method for determining cholesterol subclasses and the concentration of apolipoprotein $B_{100}$ in a sample in a single test, comprising:
   performing a cholesterol subclass measurement test on a sample by separating the sample into cholesterol subclasses wherein the concentration of at least two or more cholesterol subclasses are measured; and
   directly calculating, based on the measured concentration of the at least two or more subclasses of cholesterol from the cholesterol subclass measurement test, the concentration of apolipoprotein $B_{100}$ in the sample.

2. The method of claim 1, wherein the two or more subclasses of cholesterol further comprises a low density lipoprotein subclass, an intermediate density lipoprotein subclass, a lipoprotein (a) subclass and a very low density lipoprotein subclass.

3. The method of claim 2, wherein calculating the concentration of apolipoprotein $B_{100}$ further comprises calculating the concentration of apolipoprotein $B_{100}$ based on a particular low density lipoprotein (LDL) pattern.

4. The method of claim 3, wherein the particular low density lipoprotein pattern further comprises LDL pattern A.

5. The method of claim 3, wherein the particular low density lipoprotein pattern further comprises LDL pattern B.

6. The method of claim 3, wherein the particular low density lipoprotein pattern further comprises LDL pattern A/B.

7. The method of claim 1, wherein performing a cholesterol subclass measurement test further comprises performing a controlled dispersion flow method.

8. The method of claim 1, wherein calculating the concentration of apolipoprotein $B_{100}$ further comprises calculating, based on a value of the concentrations of the at least two or more subclasses of cholesterol, the concentration of apolipoprotein $B_{100}$ in the sample without re-testing the sample.

9. An apparatus for determining cholesterol subclasses and the concentration of apolipoprotein $B_{100}$ in a sample in a single test, comprising:
   a testing apparatus for determining the concentration of at least two or more subclasses of cholesterol in a sample by separating the sample into cholesterol subclasses and outputting the values of the concentrations of the at least two or more subclasses of cholesterol; and a computer system that, based on the measured concentration of the at least two or more subclasses of cholesterol from the testing apparatus, directly the concentration of apolipoprotein $B_{100}$ in the sample.

10. The apparatus of claim 9, wherein the two or more subclasses of cholesterol further comprises a low density lipoprotein subclass, an intermediate density lipoprotein subclass, a lipoprotein (a) subclass and a very low density lipoprotein subclass.

11. The apparatus of claim 9, wherein the testing apparatus further comprises a controlled dispersion flow testing apparatus.

12. The apparatus of claim 9, wherein the computer system further comprises a processing unit that executes a plurality of lines of computer code that calculates the concentration of apolipoprotein $B_{100}$.

13. The apparatus of claim 12, wherein the plurality of lines of computer code calculate the concentration of apolipoprotein $B_{100}$ based on a particular low density lipoprotein (LDL) pattern.

14. The apparatus of claim 13, wherein the particular low density lipoprotein pattern further comprises LDL pattern A.

15. The apparatus of claim 13, wherein the particular low density lipoprotein pattern further comprises LDL pattern B.

16. The apparatus of claim 13, wherein the particular low density lipoprotein pattern further comprises LDL pattern A/B.

17. The apparatus of claim 9, wherein the computer system calculates the concentration of apolipoprotein $B_{100}$ in the sample without re-testing the sample based on a value of the concentrations of the at least two or more subclasses of cholesterol.

* * * * *